US006191259B1

(12) United States Patent
DeMars et al.

(10) Patent No.: US 6,191,259 B1
(45) Date of Patent: Feb. 20, 2001

(54) CYTOTOXIC T LYMPHOCYTE EPITOPES OF THE MAJOR OUTER MEMBRANE PROTEIN OF CHLAMYDIA TRACHOMATIS

(75) Inventors: Robert I. DeMars; Seon-Kyeong Kim, both of Madison, WI (US)

(73) Assignee: Wisconsin Alumni Research Foundation, Madison, WI (US)

( * ) Notice: Under 35 U.S.C. 154(b), the term of this patent shall be extended for 0 days.

(21) Appl. No.: 09/314,742

(22) Filed: May 19, 1999

(51) Int. Cl.[7] ........................................................ C07K 1/00
(52) U.S. Cl. .......................... 530/350; 435/6; 536/23.1; 424/184.1; 530/350; 530/328; 530/300; 530/326
(58) Field of Search ................................. 435/6; 536/23.1; 530/328, 350, 300, 326; 424/184.1

(56) References Cited

U.S. PATENT DOCUMENTS

| | | | |
|---|---|---|---|
| 5,770,714 | * 6/1998 | Agabian et al. | 536/23.1 |
| 5,821,055 | * 10/1998 | Agabian et al. | 435/6 |
| 6,001,372 | 12/1999 | DeMars et al. | 424/263.1 |

FOREIGN PATENT DOCUMENTS

| | | |
|---|---|---|
| 0192033 | * 8/1986 | (EP) . |
| WO98/50074 | * 11/1998 | (WO) . |

OTHER PUBLICATIONS

Alignments (SEQ ID Nos. 1–6), 1998.*
L. Ortiz et al., Chlamydia Trachomatis Major Outer Membrane Protein (MOMP) Epitopes That Activate HLA Class II–Restricted T Cells From Infected Humans, 157 J. Immunol. 4554–4567 (1996).

E. Peterson et al., The Major Outer Membrane Protein Nucleotide Sequence Of Chlamydia Trachomatis, Serovar E, 18 Nuc. Acid. Res. 3414 (1990).

M. Holland et al., Synthetic Peptides Based On Chlamydia Trachomatis Antigens Identify Cytotoxic T Lymphocyte Responses In Subjects From a Trachoma–Endemic Population, 107 Clin. Exp. Immunol. 44–49 (1997).

D. Zhang et al., DNA Vaccination With The Major Outer–Membrane Protein Gene Induces Acquired Immunity To Chlamydia Trachomatis (Mouse Pneumonitis) Infection, 176 J.I.D.. 1035–1040 (1997).

S. Kim et al., HLA Class I–Restricted, CD8+ CTL Specific For Chlamydia Trachomatis MOMP Are Induced In Genital Tract Infections, 1998 Autumn Immunology Conference (1998)—not prior art.

H. Rammensee, et al., MHC Ligands And Peptide Motifs: First Listing, 41 Immunogen. 178–228 (1995).

* cited by examiner

*Primary Examiner*—Christopher S. F. Low
*Assistant Examiner*—Hope A. Robinson
(74) *Attorney, Agent, or Firm*—Quarles & Brady LLP

(57) ABSTRACT

Disclosed herein are short peptides from the major outer membrane protein of *Chlamydia trachomatis* serovar E. These fragments activate cytotoxic T-lymphocytes (CD8+). Thus, the fragments, as well as DNA coding for them, are intended for use in vaccination of humans. Also, they are useful in connection with diagnostic tests.

7 Claims, No Drawings

CYTOTOXIC T LYMPHOCYTE EPITOPES OF THE MAJOR OUTER MEMBRANE PROTEIN OF CHLAMYDIA TRACHOMATIS

This invention was made with United States government support awarded by the following agency: NIH A134617. The United States has certain rights in this invention.

CROSS REFERENCES TO RELATED APPLICATIONS

STATEMENT REGARDING FEDERALLY SPONSORED RESEARCH

Not applicable.

BACKGROUND OF THE INVENTION

The present invention relates to peptide fragments of the major outer membrane protein ("MOMP") from *Chlamydia trachomatis*. These peptides activate cytotoxic T-lymphocytes ("CTL").

*Chlamydia trachomatis* ("Ct") is an intracellular bacterium that is the leading cause of preventable infectious blindness (ocular trachoma) in the developing world and of sexually transmitted disease ("STD") in the United States and certain other parts of the developed world. The estimated annual incidence of Ct-caused STD is in the millions. While most Ct caused disease can be treated with antibiotics, untreated or inadequately treated infections result in hundreds of thousands of cases of pelvic inflammatory disease each year in the United States, alone.

Adverse outcomes of pregnancy, ectopic pregnancy and tubal infertility are among the consequences. Moreover, apparent clearance of infection by a given serovar (serologically distinct strain of Ct) can be followed by the infection becoming latent and prolonged or by reinfection. This is important because much Ct-caused pathology results from tissue-damaging inflammatory responses of the immune system that are triggered by repeated or prolonged exposures to the whole organism. Therefore, there is a need for improved means to prevent primary infections.

Complicating matters is the fact that humans have a variety of HLA types, these types determining the specific parts of Ct antigens to which an individual's immune system can respond. What can provoke such a response for one human HLA type, may not do so for others. This is a particularly troubling problem for those seeking to develop vaccines for the human population in general.

Where a particular peptide provokes an immune response from only a portion of the population, there is thus a need to identify one or more peptides that provoke a response from the remainder of the population. Thus, it has been proposed to create a "cocktail" type sub-unit vaccine containing multiple such fragments.

Using whole MOMP is not a good solution. Whole MOMP is too difficult to isolate from natural CT cultures in large quantities that are sufficiently pure for use in mass vaccination. Larger quantities of recombinant MOMP could theoretically be produced in *E. coli*, but the chemical properties (e.g. insolubility except in detergents) impede its large scale preparation as a non-toxic vaccine. Furthermore, use of whole MOMP has too much risk of adverse side effects.

To date there have been a number of reports regarding attempts to develop vaccines based on multiple or single MOMP fragments where the focus is on raising T-cell and/or B-cell antigenic responses (often in mice, but in some cases in human cells). See H. Su et al., 172 J. Exp. Med. 203–212 (1990) (serovar A); J. Allen et al., 147 J. Immunol. 674–679 (1991) (serovar B); M. Ishizaki et al., 60 Infect. & Immun. 3714–3718 (1992) (serovars B, C); G. Zhong et al., 151 J. Immunol. 3728–3736 (1993) (serovar B). L. Ortiz et al. 157 J. Immunol. 4554–4567 (1996) (serovar E) and U.S. Pat. No. 6,001,372. The disclosure of these publications and of all other publications referred to herein are incorporated by reference as if fully set forth herein.

The amino acid sequence of serovar B of MOMP is also disclosed in L. Ortiz et al. 157 J. Immunol. 4554–4567 (1996). The naturally occurring DNA coding sequence of serovar E of MOMP is disclosed in E. Peterson et al., 18 Nuc. Acids. Res. 3414 (1990). Sequence analysis of MOMP from a variety of sources has revealed that slight amino acid sequence variation between serovars of MOMP accounts for the antigenic diversity of this pathogen. See generally M. Ishizaki et al., 60 Infect. & Immun. 3714–3718 (1992).

As such, any sub-unit vaccine preferably relies on peptide fragments that are in regions that are conserved between serovars (or at least in conserved regions of those serovars which are of the greatest interest). Subunit vaccines based on such conserved peptide sequences are potentially useful for vaccinating a large population of individuals.

Recently there has been a description in M. Holland et al., 107 Clin. Exp. Immunol. 44–49 (1997) of certain synthetic peptides that had a limited cytotoxic T-lymphocyte response with respect to populations having the HLA B8 and/or B35 typing who had been exposed to trachoma. However, such a CTL response was detectable in less than 10% of infected people tested. Even when detectable, the killing activity of the CTL was reported to be low.

Apart from vaccine utility, it is desirable to find peptides that can be used as components of diagnostic tests (e.g. to confirm the presence of the disease once a positive test result has been obtained using conventional tests).

As such, a need exists for the identification of peptides that provide improved sub-unit vaccines and diagnostic tests.

BRIEF SUMMARY OF THE INVENTION

In one aspect the invention provides a peptide of 8 to 10 amino acid sequences comprising an amino acid sequence selected from the group consisting of SEQ ID NO: 1, SEQ ID NO: 2, SEQ ID NO: 3, SEQ ID NO: 4, SEQ ID NO: 5, and SEQ ID NO: 6.

In another aspect, the invention provides nucleotide sequences for expressing such peptides. Such nucleotide sequences are preferably those that incorporate the applicable coding portion for the fragment of the natural MOMP gene, as described in E. Peterson et al., 18 Nuc. Acids. Res. 3414 (1990).

In yet another form, the invention provides vaccines containing such peptides or nucleotide sequences. The vaccines are capable of raising an immunological response in humans so as to increase the capacity of humans to resist adverse symptomatic development resulting from *Chlamydia trachomatis* infection.

Surprisingly, it has been learned that 8 to 10 mers of such peptides, wherein the end amino acids are compatible with desired HLA types, can trigger cytotoxic T-lymphocyte activation. This provides CTLs primed for MOMP from *Chlamydia trachomatis*.

Moreover, the capability to detect MOMP peptide-specific CTLs in peripheral blood of infected people provides a diagnostic tool. If a conventional diagnostic test based on T helper-cell or B-cell antigenic response provides a positive initial result, false positives or negatives can be screened out by then checking a blood sample using CTL activation as the indicator.

The objects of the present invention therefore include providing:

(a) peptides that can activate human CTLs; and (b) genes coding for such peptides. These and still other objects and advantages of the present invention will be apparent from the description which follows. The following description is merely of the preferred embodiments. Thus, the claims should be looked to in order to understand the full scope of the invention.

DETAILED DESCRIPTION

General Overview

We have discovered that HLA class I-restricted $CD8^+$ CTLs specific for the MOMP of *Chlamydia trachomatis* are present in the peripheral blood of humans who acquired genital tract infections with the organism. Three HLA-A2-restricted epitopes, two HLA-B51-restricted epitopes, and one HLA-B62-restricted epitope have been identified in serovar E-MOMP. One of the six epitopes spans a variable (non-conserved) segment of MOMP and is likely a serovar E-specific epitope. The other five epitopes are localized in conserved segments.

In tests relating to five of the segments, CTL populations specific for one or more of the four constant segment epitopes tested were isolated from all infected subjects tested, regardless of infecting serovars.

The CTLs failed to recognize corresponding peptides derived from *C. pneumoniae* MOMP, further suggesting that they indeed resulted from genital tract infections with *C. trachomatis*. Significantly, ME180 human cervical epithelial cells productively infected with *C. trachomatis* were lysed by the MOMP peptide-specific CTLs.

Materials And Methods

Human subjects who had recent symptomatic genital tract infections with *Chlamydia trachomatis* ("Ct") were recruited. All the infected STD subjects were treated with an oral dose of azithromycin upon confirmation of Ct infection. HLA-A2$^+$ purportedly uninfected control subjects were recruited from the similar age group. Control subjects had been sexually active, but lacked previous history of genital tract infections with Ct.

HLA class I typing was performed by PCR-sequence specific primer amplification, using Class I ABC SSP Unitray kit (Pel-Freez Clinical Systems, Brown Deer, Wis.).

B lymphoblastoid cell lines (LCLs) were established from human subjects by transformation of peripheral blood lymphocytes ("PBLs") with EBV. The HLA class I mutant cell lines used as targets in CTL assays were derived from LCL 721. Mutants LCL.45 and LCL.19 were derived by mutagenizing LCL 721 with gamma rays and by using complement plus appropriate antibodies to select for HLA deletion mutants. Further mutagenesis produced mutant LCL.144, which is HLA-A-null due to a homozygous deletion at the locus. Similarly, HLA-B-null mutant LCL.53 was derived from LCL.19 as a result of intragenic deletion at the locus. LCLs were cultured at 37° C., in humidified 5% $CO_2$ in '2/1 RPMI'; RPMI 1640 (85%) supplemented with fetal calf serum (5%), defined/supplemented calf serum (10%), 25 mM HEPES, 44 mM $NaHCO_3$, 2 mM L-glutamine, 100 U/ml penicillin and 100 µg/ml streptomycin sulfate.

ME180 human epithelioid cervical carcinoma cells (HLA-A1, A32, B8 and B44 according to PCR-based typing at the Tissue Typing Laboratory, Madison, Wis.) were used as a model for female genital tract epithelial cells. ME180 cells were cultured in MEM containing 10% fetal calf serum, 100 µM non-essential amino acids, 25 mM HEPES, 44 mM $NaHCO_3$, 100 U/ml penicillin and 100 µg/ml streptomycin sulfate. ME180 cells expressing an HLA-A1 (ME180[A1]), HLA-A2 (ME180[A2]), or HLA-B51 transgene (ME180[B51]) were prepared by introducing into ME180 cells the RSV.5neo vector carrying the genomic HLA-A*0101, HLA-A*0201, or HLA-B51*01 gene. Stable transferent cells were selected for resistance to G-418 sulfate (500 µg/ml).

Human T cells were grown at 37° C. in humidified 5% $CO_2$ using DMEM containing 4.5 g/L glucose and supplemented with 10% pooled AB-negative human serum, 100 µM non-essential amino acids, 25 mM HEPES, 44 mM $NaHCO_3$, 2 mM L-glutamine, 100 U/ml penicillin and 100 µg/ml streptomycin sulfate. When needed, recombinant human IL-2 (rhIL-2) was added at 25 U/ml. Human serum was purchased from Pel Freez (Brown Deer, Wis.), and bovine sera were purchased from Hyclone Laboratories (Logan, Utah). All tissue culture media and reagents were purchased from Gibco-BRL (Grand Island, N.Y.). All other chemicals were purchased from Sigma (St. Louis, Mo.).

Peptide Synthesis

Nine-mer peptides in accordance with SEQ ID NOS: 1–6 possessing the known binding motifs for the terminal of HLA-A2 (or HLA-B51 or HLA-B62) were identified in the mature Ct serovar-E MOMP sequence. *C. pneumoniae* (Cpn) MOMP peptides were made according to the published amino acid sequences.

Peptides were synthesized at the University of Wisconsin Biotechnology Center (Madison, Wis.) by F-moc chemistry. F-moc chemistry is described in G. A. Grant Synthetic Peptides: A User's Guide, W. H. Freeman and Co. (1992). Identities of peptides were confirmed by amino acid analysis and matrix-assisted laser desorption/ionization mass spectrometry. Lyophilized peptides were dissolved in DMSO at 20 mM, aliquotted and stored at −80° C. Peptides were diluted to 4 mM with serum-free culture medium and used at desired final concentrations.

Ct MOMP peptides that can bind to HLA-A2 molecules were identified by their ability to increase the expression of HLA-A2 on the surface of TAP-deficient mutant cell line LCL.174. Briefly, LCL.174 was plated in a round-bottomed 96-well plate at 2×b 10 cells/well in 200 µl of 2/1 RPMI together with 50 µM of peptide and incubated overnight at 37° C. The cells were then stained with HLA-A2-specific mAb, BB7.2 (ATCC, Rockville, Md.), followed by FITC-conjugated goat anti-mouse IgG. Fluorescence intensity was analyzed by flow cytometry. Influenza virus matrix M1 protein peptide, FluMP58, is a known HLA-A2-restricted CTL epitope and used as a positive control. Hepatitis B virus envelope antigen peptide, HBenvAg125, does not bind to HLA-A2 and was used as a negative control.

Stimulation Of CTLs

PBMCs were prepared from ~30 ml of heparinized peripheral blood obtained from human subjects by centrifugation over Ficoll-Hypaque (Sigma, St. Louis, Mo.). $CD8^+$ cells were positively selected from freshly isolated peripheral blood mononuclear cells ("PBMCs"), or sometimes from PBMCs frozen in liquid $N_2$, using anti-CD8 magnetic microbeads according to the manufacturer's instructions (Milteny Biotec, Auburn, Calif.).

Negatively selected cells were resuspended in serum-free DMEM and plated in 500 µl aliquots into 48 well plates at $3 \times 10^6$ cells/well. After 2 hr at 37° C., 5% $CO_2$, non-adherent cells were removed by repeated washing, and adherent monocytes were incubated for 4 hr with 50 µM peptide and 5 µg/ml human $\beta_2$-microglobulin (Sigma, St. Louis, Mo.). After being washed with serum-free DMEM, each well received $1.5 \times 10^6$ CD8$^+$ cells (>90% pure by flow cytometry) in 500 µl of DMEM containing 10% human serum supplemented with rhIL-7 (0.5 ng/ml; R&D Systems, Minneapolis, Minn.).

rhIL-2 was given at 25 U/ml after 2 days and twice a week thereafter by replacing half of the culture medium. On day 10, CTL cultures were restimulated at a responder to stimulator ratio of 5 with irradiated (5000 rad), autologous LCLs incubated with 20 µM peptide. Alternatively, LCL.174 incubated with 50 µM peptide was used to restimulate CTL cultures obtained from HLA-A2$^+$ subjects. CTL assays were performed a week after restimulation as described below.

Peptide-stimulated CTLs could be frozen after initial characterization in medium that consisted of 30% human serum, 10% DMSO and 60% DMEM, and then thawed and restimulated for further analysis. Influenza virus matrix M1 protein peptide, FluMP58, was used as a positive control for in vitro stimulation of peptide-specific CTLs.

CTL Assays

Cytolytic activity of peptide-stimulated CTL cultures was assessed in [$^3$H]thymidine release assays or in [$^3$H]uridine release assays. Target LCLs ($3 \times 10^5$ cells/ml) were labeled overnight with [$^3$H]thymidine (2.0 Ci/mmol; New England Nuclear, Boston, Mass.) or with [$^3$H]uridine (25~30 Ci/mmol; Amersham, Arlington Heights, Ill.) at 10 µCi/ml, while in growth phase. After 1 hr incubation with or without 10 µM peptide, the target cells were washed three times to remove excess peptides. 5000 target cells were then plated in round-bottomed wells of 96-well plates along with different numbers of CTLs in a total volume of 200 µl of 2/1 RPMI to give desired E:T ratios.

After 6 hr at 37° C., 100 µl of supernatant was harvested from each well, air-dried on glass fiber filters and counted in a liquid scintillation counter. Spontaneous release was determined for target cells in medium alone. Maximal labeling was determined from the equivalent wells by taking 100 µl after thoroughly mixing the contents of the wells. Maximal labeling was 3000–5000 cpm for [$^3$H]thymidine-labeled LCLs, and 6000–8000 cpm for [$^3$H]uridine-labeled LCLs. Spontaneous release was typically 5–10% of maximal labeling. When ME180 cells were used as targets, adherent cells were incubated overnight with radioactive labels as described above. Cells were then trypsinized and incubated for 1 hr with or without 10 µM peptide before being plated together with CTLs.

Maximal labeling was 5000–6000 cpm for [$^3$H]thymidine-labeled ME180 cells, and ~10,000 cpm for [$^3$H]uridine-labeled ME180 cells. Spontaneous release was usually 5–10% of maximal labeling.

Chlamydia-Infected Target Cells

Serovar E/UW-5 genital strain of *Chlamydia trachomatis* was obtained, grown in HeLa cells and purified by density gradient centrifugation as previously described. The purified elementary bodies (EBs) were resuspended in SPG (sucrose-phosphate-glutamic acid buffer) and stored at −80° C. until use. Inclusion forming units (IFUs) of purified organisms were assayed on HeLa cells by indirect fluorescent-antibody staining as previously described. ME180 and ME180[A2] cells were maintained without antibiotics until they were inoculated with Ct.

Cells were seeded at $3 \times 10^5$ cells/well in a 12-well plate (Costar, New York, N.Y.) together with 10 µCi/ml [$^3$H] uridine. 24 hr later, the subconfluent monolayers were washed twice with PBS and inoculated with live, heat-killed or UV-killed EBs at a multiplicity of infection (MOI) of 10 (i.e. 10 IFUs per cell) in 500 µl of SPG for 2 hr at 37° C. Heat-killed EBs were prepared by incubating them in a 56° C. water bath for 30 min, and UV light-inactivated EBs by exposing the organisms to a 30 W UV source (10 erg/sec, General Electric, Fairfield, Conn.) at a distance of 10 cm for 30 min.

Live EBs and killed EBs were used at equal dilutions. Inoculum was removed by washing, and infected cells were cultured for 24 hr or for 48 hr in antibiotic-free RPMI 1640 containing 10% fetal calf serum before use in CTL assays. Uninfected cells were treated with SPG alone, incubated for the same amount of time and used as a control in CTL assays.

CTL assays were performed with 5,000 infected cells per well at an E:T ratio of 50 as described above. Spontaneous release from infected cells was ~10% of maximum labeling at 24 hr post-infection and 15–20% at 48 hr post-infection. At 72 hr post-infection, 60–70% of infected cells spontaneously lysed, and was excluded from our experiments. Essentially all cells were lysed by 96 hr after infection with live EBs. Spontaneous release from cells incubated with killed organisms remained similar (~10% of maximal labeling) up to 96 hr post-inoculation.

Results

We initially chose to examine Ct MOMP-specific CTL responses restricted by HLA-A2, HLA-B51, and HLA-B62, which are among the most common HLA alleles found in various ethnic populations. Out of sixteen Ct-infected subjects who enrolled in our research program, nine were typed to be HLA-A2$^+$, three were typed to be HLA-B51$^+$; and three were typed to be HLA-B62$^+$.

Synthetic peptides derived from MOMP of Ct serovar E were used to stimulate outgrowth of CD8$^+$ T cells obtained from peripheral blood of Ct-infected human subjects. Serovar E was chosen for the study, because it is one of the most common causes of human genital tract infections. MOMP peptides possessing a proposed HLA-A2-binding motif were tested for their ability to bind to HLA-A2 molecules.

SEQ ID NOS: 1, 2 and 3 were identified as binders of this HLA type, and were subsequently used for in vitro stimulation of CD8$^+$ cells obtained from HLA-A2$^+$ subjects.

Peptides possessing an HLA-B51-binding motif were used in stimulation of CD8$^+$ cells from HLA-B51$^+$ subjects (without performing preliminary peptide binding assays). SEQ ID NOS: 4 and 5 were identified as binders of this HLA type, and were subsequently used for in vitro stimulation of CD8$^+$ cells obtained from HLA-B51$^+$ subjects.

Similar experiments have been done with respect to SEQ ID NO: 6 vis a vis HLA-B62.

To confirm that the MOMP peptide-specific CTLs described above were indeed elicited by genital tract infections with Ct, HLA-A2⁺ uninfected subjects were recruited and their CD8⁺ T cells were stimulated in vitro with peptides SEQ ID NOS: 1 and 2 following the same protocol used for infected subjects. The cytolytic activity of CTL cultures was assessed in [$^3$H]thymidine release and [$^3$H]uridine release assays performed in parallel, using HLA-A2⁺ LCL.53 as targets.

Five of six uninfected control subjects had no detectable CTL activity against the two peptides, while one had CTL populations specific for both peptides. We later found out that the purported control subject that showed a positive test had acquired influenza infection shortly before a blood sample was taken for this experiment. Thus, our peptides can serve as an important diagnostic tool, e.g. a backup check for false positives or false negatives.

An additional control subject (HLA-A2⁺ and HLA-B51⁺) was tested with HLA-B51-restricted CTL epitopes, SEQ ID NOS: 4 and 5, as well as with HLA-A2-restricted CTL epitopes. None of these peptides stimulated CTLs in this subject.

We also investigated whether human genital tract epithelial cells presenting appropriate MOMP peptide epitopes would be susceptible to lysis by MOMP peptide-specific CTLs. The CTLs specific for MOMP peptides were obtained from HLA-A2⁺ and HLA-B51⁺ infected subjects, and their cytolytic activity was first assessed using LCLs as targets in [$^3$H]thymidine release assays. ME180 human cervical epithelial cell and its transferent cells expressing an HLA-A2 (ME180[A2]) or a HLA-B51 (ME180[B51]) transgene were subsequently used as targets.

Interestingly, the lysis of ME180 cells by the CTLs was not detectable with [$^3$H]thymidine release (data not shown), but was detectable with [$^3$H]uridine release. When incubated with appropriate peptides, ME180[A2] cells were clearly susceptible to lysis by HLA-A2-restricted CTLs specific for SEQ ID NOS: 1–3.

Mechanisms of cytotoxicity caused by CTLs in cervical epithelial cells and B cells are different. CTLs appear to induce the death of cervical epithelial cells via cell membrane disintegration (detectable by [$^3$H]uridine release) without causing pre-lytic DNA fragmentation (detectable by [$^3$H]thymidine release). In contrast, B cells are susceptible to both cell death pathways. The lysis of target LCLs by FluMP58-specific CTLs detected by [$^3$H]uridine release was comparable to that assessed by [$^3$H]thymidine release in 6 hr CTL assays.

Diagnostic Protocols

It will be appreciated that instead of using known blood samples, samples whose infection status is not known can be tested via the above techniques.

Vaccine Protocol-A

In sterile dropper bottle the suspending medium is sterile phosphate-buffered saline. Some or all of SEQ ID NOS: 1–6 is present at 4 mg/ml. Cholera toxin subunit B at 2 mg/ml is also present to enhance immune responses at mucosal surfaces, which are the sites at which Ct multiply and cause pathology. Use of subunit B has been safely tested with humans in other contexts.

To administer to a human, one shakes well, and uses two drops (about 0.1 ml) in each nostril and each eye. Administration should preferably be on days 0, 7 and 14. T and/or B cell epitope peptides may also optionally be included, as may booster applications.

Vaccine Protocol-B

The proposed vaccine agent is an attenuated bacterial strain of *Salmonella typhimurium* bearing a replicating plasmid into which is inserted DNA sequences capable of expressing the peptides of interest in vivo. We propose as a vector attenuated *Salmonella typhimurium* strain $_{\chi}$4072. See F. Schödel et al., 62 Infect. and Immun. 1669–1676 (1994) which has Δ crp-1 and Δ cya mutations that render it avirulent and a Δ asdA-1 mutation that renders it inviable unless a normal asdA gene is present on an indwelling plasmid.

Plasmid pYAN is a form of pYA292 that is modified to have a Nco I site. See Schödel et al., supra. The presence of the Nco I site allows in frame insertion of the AUG of the foreign protein of interest into the plasmid. pYAN lacks antibiotic resistance genes, allowing use of antibiotics should symptoms suggestive of Salmonella pathology appear.

pYAN does have a normal asda gene, which maintains viability of only those bacteria that retain the plasmid. A DNA sequence is synthesized encoding an AUG followed by the sequences encoding the peptide. The suggested dose is $5\times10^4$ colony forming units for small children and $5\times10^5$ colony forming units for adults.

For adults, the bacteria will be administered with sodium bicarbonate (2 g of $NaHCO_3$ in 150 ml of distilled water). One should first drink 120 ml of the solution to neutralize gastric acid. One minute later, one drinks the remaining 30 ml of bicarbonate solution, now containing the bacteria. No food or drink is permitted for 90 minutes before or after vaccination.

Vaccine Protocol-C

Alternatively, the DNA may be delivered by other DNA delivery techniques such as those analogous to the vaccination protocol described in D. Zhang et al., 176 J.I.D. 1035–1040 (1997).

While the preferred embodiments have been described above, it will be appreciated by those skilled in the art that other modification can be made within the scope of the invention. For example, instead of expressing the DNA in *E. coli*, one might optimize the DNA for other hosts and express it in those hosts.

Further, while six specific sequences have been identified, it is believed that the techniques of the present invention can be utilized to identify other desired 8–10 mers having desirable CTL activation characteristics. Thus, the claims should be looked to in order to judge the full scope of the invention.

Industrial Applicability

The invention provides peptides and DNA that can be used for diagnostic and vaccination purposes.

We claim:

1. A peptide of 9 to 10 amino acid residues that is separate from a *Chlamydia trachomatis* bacterial cell and a human cell, the peptide being capable of activating cytotoxic T-lymphocytes, the peptide comprising an amino acid sequence selected from the group consisting of SEQ ID NO: 1, SEQ ID NO: 2, SEQ ID NO: 3, SEQ ID NO: 4, SEQ ID NO: 5, and SEQ ID NO: 6, wherein the peptide does not have more than 10 amino acid residues.

2. The peptide of claim 1, wherein the amino acid sequence that is selected is SEQ ID NO: 1.

3. The peptide of claim 1, wherein the amino acid sequence that is selected is SEQ ID NO: 2.

4. The peptide of claim 1, wherein the amino acid sequence that is selected is SEQ ID NO: 3.

5. The peptide of claim 1, wherein the amino acid sequence that is selected is SEQ ID NO: 4.

6. The peptide of claim 1, wherein the amino acid sequence that is selected is SEQ ID NO: 5.

7. The peptide of claim 1, wherein the amino acid sequence that is selected is SEQ ID NO: 6.

* * * * *

UNITED STATES PATENT AND TRADEMARK OFFICE
CERTIFICATE OF CORRECTION

PATENT NO.   : 6,191,259 B1                                            Page 1 of 1
DATED        : February 20, 2001
INVENTOR(S)  : Robert I. Demars; Seon-Kyeong Kim It is certified that error appears in the above-identified patent and that said Letters Patent is hereby corrected as shown below:

Column 1,
Line 11, (in the section regarding sponsored research) delete [Not applicable.], and move the paragraph at line 4, column 1 (that begins with "This invention ...") to the position where "Not applicable." previously was.

Column 2,
Line 7, immediately following "6,001,372" add -- (serovar E). --
Line 10, replace "[serovar B]" with -- serovar E. --

Column 4,
Line 52, replace "[2xb]" with -- 2x. --

Signed and Sealed this

Eighth Day of January, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,191,259 B1
DATED         : February 20, 2001
INVENTOR(S)   : Robert I. DeMars and Seon-Kyeong Kim It is certified that error appears in the above-identified patent and that said Letters Patent is hereby corrected as shown below:

<u>Column 9, lines 62-67 and Column 10, lines 61 & 62,</u>
Replace claim 1 with the following:
-- A purified peptide of 9 to 10 amino acid residues that activates cytotoxic T-lymphocytes, the peptide comprising an amino acid sequence selected from the group consisting of SEQ ID NO: 1, SEQ ID NO: 2, SEQ NO: 3, SEQ ID NO: 4, SEQ ID NO: 5, and SEQ ID NO: 6, wherein the peptide does not have more than 10 amino acid residues. --

Signed and Sealed this

Twenty-fourth Day of December, 2002

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 9
<212> TYPE: PRT
<213> ORGANISM: Chlamydia trachomatis

<400> SEQUENCE: 1

Ser Leu Asp Gln Ser Val Val Glu Leu
 1               5

<210> SEQ ID NO 2
<211> LENGTH: 9
<212> TYPE: PRT
<213> ORGANISM: Chlamydia trachomatis

<400> SEQUENCE: 2

Arg Leu Asn Met Phe Thr Pro Tyr Ile
 1               5

<210> SEQ ID NO 3
<211> LENGTH: 9
<212> TYPE: PRT
<213> ORGANISM: Chlamydia trachomatis

<400> SEQUENCE: 3

Asn Met Phe Thr Pro Tyr Ile Gly Val
 1               5

<210> SEQ ID NO 4
<211> LENGTH: 9
<212> TYPE: PRT
<213> ORGANISM: Chlamydia trachomatis

<400> SEQUENCE: 4

Asn Ala Ala Cys Met Ala Leu Asn Ile
 1               5

<210> SEQ ID NO 5
<211> LENGTH: 9
<212> TYPE: PRT
<213> ORGANISM: Chlamydia trachomatis

<400> SEQUENCE: 5

Asp Ala Asp Lys Tyr Ala Val Thr Val
 1               5

<210> SEQ ID NO 6
<211> LENGTH: 9
<212> TYPE: PRT
<213> ORGANISM: Chlamydia trachomatis

<400> SEQUENCE: 6

Trp Gln Ala Ser Leu Ala Leu Ser Tyr
 1               5